United States Patent
Iijima et al.

(10) Patent No.: US 10,982,054 B2
(45) Date of Patent: Apr. 20, 2021

(54) POLYMER GEL AND PREPARATION METHOD THEREFOR

(71) Applicant: SAMSUNG ELECTRONICS CO., LTD., Suwon-si (KR)

(72) Inventors: Kazuo Iijima, Kanagawa (JP); Jian Ping Gong, Sapporo (JP); Yukiko Hane, Sapporo (JP); Takayuki Kurokawa, Sapporo (JP)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 222 days.

(21) Appl. No.: 15/538,478

(22) PCT Filed: Dec. 25, 2015

(86) PCT No.: PCT/KR2015/013991
§ 371 (c)(1),
(2) Date: Jun. 21, 2017

(87) PCT Pub. No.: WO2016/105039
PCT Pub. Date: Jun. 30, 2016

(65) Prior Publication Data
US 2017/0342220 A1    Nov. 30, 2017

(30) Foreign Application Priority Data

Dec. 26, 2014 (JP) .................... JP2014-266081
Sep. 25, 2015 (KR) .................... 10-2015-0137082

(51) Int. Cl.
| | | |
|---|---|---|
| C08J 3/075 | (2006.01) | |
| C08F 2/10 | (2006.01) | |
| C08F 2/56 | (2006.01) | |
| C08J 9/28 | (2006.01) | |
| A61B 8/00 | (2006.01) | |

(52) U.S. Cl.
CPC .............. C08J 3/075 (2013.01); C08F 2/10 (2013.01); C08F 2/56 (2013.01); C08J 9/28 (2013.01); *A61B 8/44* (2013.01); *A61B 8/4444* (2013.01); *A61B 8/4483* (2013.01); *C08J 2201/026* (2013.01); *C08J 2205/022* (2013.01); *C08J 2205/04* (2013.01); *C08J 2207/10* (2013.01); *C08J 2300/14* (2013.01); *C08J 2300/208* (2013.01); *C08J 2333/26* (2013.01)

(58) Field of Classification Search
CPC ....... A61B 8/4444; A61B 8/44; A61B 8/4483; C08J 3/075; C08J 2300/208
See application file for complete search history.

(56) References Cited

U.S. PATENT DOCUMENTS

| | | | | |
|---|---|---|---|---|
| 4,374,933 A * | 2/1983 | Scholze | ................ | B01D 71/70 |
| | | | | 210/500.33 |
| 4,645,698 A | 2/1987 | Matsubara | | |
| 5,494,038 A * | 2/1996 | Wang | ................ | A61B 8/0866 |
| | | | | 600/459 |
| 5,856,370 A | 1/1999 | Chmelir | | |
| 6,268,405 B1 * | 7/2001 | Yao | ................ | A61L 27/16 |
| | | | | 264/28 |
| 6,623,450 B1 * | 9/2003 | Dutta | ................ | A61F 2/01 |
| | | | | 604/48 |
| 8,029,824 B2 | 10/2011 | Osada et al. | | |
| 8,795,709 B2 | 8/2014 | Sawhney et al. | | |
| 2003/0146145 A1 * | 8/2003 | Krotz | ................ | B01D 67/003 |
| | | | | 210/243 |
| 2003/0232895 A1 | 12/2003 | Omidian et al. | | |
| 2004/0116305 A1 | 6/2004 | Osada et al. | | |
| 2006/0068014 A1 | 3/2006 | Munro et al. | | |
| 2016/0200891 A1 * | 7/2016 | Virgilio | ................ | C08J 9/26 |
| | | | | 424/492 |

FOREIGN PATENT DOCUMENTS

| | | | |
|---|---|---|---|
| JP | 2004-027195 | A | 1/2004 |
| JP | 2005-526879 | A | 9/2005 |
| JP | 2008-280406 | A | 11/2008 |
| JP | 4381297 | B2 | 12/2009 |
| JP | 5048183 | B2 | 10/2012 |
| KR | 10-1992-0001014 | B1 | 2/1992 |
| KR | 10-2005-0043099 | A | 5/2005 |
| WO | 03/093337 | A1 | 11/2003 |

OTHER PUBLICATIONS

Jinkun Hao, R.A. Weiss, "Mechanical behavior of hybrid hydrogels composed of a physical and a chemical network", Polymer, 54, 2013, pp. 2174-2182.
Fuat Topuz, et al., "Macroporous hydrogel beads of high toughness and superfast responsivity", Reactive & Functional Polymers, 69, 2009, pp. 273-280.
M. Murat Ozmen, et al., "Preparation of Macroporous Acrylamide-based Hydrogels: Cryogelation under Isothermal Conditions", Journal of Macromolecular Science, Part A: Pure and Applied Chemistry, 2007, 44, pp. 1195-1202.
Ashok Kumar, et al., "Cell separation using cryogel-based affinity chromatography", Nature Protocols, vol. 5, No. 11, Oct. 7, 2010, total 12 pages.
International Search Report (PCT/ISA/210) and Written Opinion (PCT/ISA/237) dated Mar. 28, 2016 issued by the International Searching Authority in counterpart International Application No. PCT/KR2015/013991.
Communication dated Nov. 13, 2018, issued by the Japanese Patent Office in counterpart Japanese Application No. 2014-266081.

\* cited by examiner

*Primary Examiner* — James W Rogers
(74) *Attorney, Agent, or Firm* — Sughrue Mion, PLLC

(57) ABSTRACT

When a polymer gel has excellent mechanical strength and an ability to maintain surface wetness for a longer time, the polymer gel may be very widely applied to a variety of fields. The present disclosure provides example embodiments of a polymer gel having excellent mechanical strength and an ability to maintain surface wetness for a longer time. Further, the present disclosure provides example embodiments of a method of preparing the polymer gel.

21 Claims, 4 Drawing Sheets

US 10,982,054 B2

POLYMER GEL AND PREPARATION METHOD THEREFOR

TECHNICAL FIELD

The present disclosure relates to a polymer gel, and a method of preparing the same.

BACKGROUND ART

Generally, a polymer gel refers to a material including a three-dimensional network structure formed by crosslinked polymer chains; and a liquid held in the three-dimensional network structure. A polymer gel may be applied to a wide variety of fields, for example, from food materials such as agar or gelatin to medical materials such as contact lenses. Due to its non-uniform network structure, a polymer gel generally has very low mechanical strength and its industrial applications are limited, but polymer gel materials having various functions have been proposed.

For example, Patent Document 1 discloses a double-network gel material having increased mechanical strength. Non-Patent Document 1 discloses a hybrid hydrogel composed of a physical network and a chemical network, the physical network being derived from a nanophase-separated microstructure of hydrophobic nanodomains, and the chemical network which is crosslinked with cinnamoyl moieties. Non-Patent Document 2 discloses hydrogel beads prepared at a temperature of −15° C.~−20° C.: the prepared hydrogel beads release water under pressure of a piston and a shape thereof is recovered when the pressure is released and water is added. Non-Patent Document 3 discloses a hydrogel which is polymerized in a reaction mixture containing hydroquinone as a polymerization inhibitor: this reaction mixture is cooled to −196° C., and then heated to a desired temperature. Non-Patent Document 4 discloses chromatography using a cryogel.

Patent Document 1: International Patent Publication NO. 2003/093337
Non-Patent Document 1: Weiss, R. A. et al.; Polymer 2013, 54, 2174-2182
Non-Patent Document 2: Okay, O. et al.; Reactive & Functional Polymers 2009, 69, 273-280.
Non-Patent Document 3: Okay, O. et al.; Macromol. Sci., Part A., 2007, 44, 1195-1202.
Non-Patent Document 4: Srivastava, A. et al.; Nature Protocols 2010, 5, 1737-1747.

DETAILED DESCRIPTION OF THE INVENTION

Technical Problem

A polymer gel has an advantage in that it may hold therein a high content of a solvent, for example, water. However, the surface of a polymer gel, when left in the air, does not maintain its wet state and dries rapidly. A polymer gel having a dried surface has very limited applications. If a polymer gel has excellent mechanical strength and also has an ability to maintain surface wetness for a longer time, the polymer gel may be widely applied to a variety of fields. The present disclosure provides example embodiments of a polymer gel having excellent mechanical strength and an ability to maintain surface wetness for a longer time. Further, the present disclosure provides example embodiments of a method of preparing the polymer gel.

Technical Solution

An example embodiment of a polymer gel according to a first aspect of the present disclosure is a polymer gel including a polymeric three-dimensional network structure, in which the polymeric three-dimensional network structure includes a solvent holding pore and a solvent exuding pore, the solvent exuding pore has a larger size than the solvent holding pore, and the solvent exuding pore exudes a solvent included in the solvent exuding pore to at least one surface of the polymer gel when mechanical energy is applied to the polymer gel.

In another example embodiment of the polymer gel of the present disclosure, the solvent exuding pore may have a pore size of 3 mm or less.

In still another example embodiment of the polymer gel of the present disclosure, the solvent exuding pore may have a pore size of 0.5 mm or less.

In still another example embodiment of the polymer gel of the present disclosure, the solvent exuding pore may have a pore size of 0.5 µm or more.

In still another example embodiment of the polymer gel of the present disclosure, the solvent exuding pore may have a pore size of 2 µm or more.

In still another example embodiment of the polymer gel of the present disclosure, work required to elongate the polymer gel may be 3,000 J/m$^3$, as measured in a state attained by swelling the polymer gel including a solvent until equilibrium.

In still another example embodiment of the polymer gel of the present disclosure, the polymer gel may be a hydrogel including water as the solvent.

In still another example embodiment of the polymer gel of the present disclosure, the mechanical energy may be at least one of a compressive force and an ultrasonic wave.

In still another example embodiment of the polymer gel of the present disclosure, the polymeric three-dimensional network structure may have an interpenetrating network structure of a plurality of polymeric three-dimensional network structures which are entangled with each other.

In still another example embodiment of the polymer gel of the present disclosure, a content of the solvent in the polymer gel may be 80% by weight or less, based on 100% by weight of a maximum solvent content of the polymer gel.

An example embodiment of a method of preparing a polymer gel according to a second aspect of the present disclosure includes (A) preparing the polymer gel including a solvent and a polymeric three-dimensional network structure holding the solvent, wherein hydrogen bonding functional groups are included in the three-dimensional network structure or between three-dimensional network structures; and (B) freezing and solidifying at least a portion of the solvent included in the polymer gel, wherein a solvent holding pore that holds the solvent even when mechanical energy is applied is formed by Step (A), and a solvent exuding pore that actively exudes the solvent when mechanical energy is applied is formed by Step (B).

An example embodiment of a method of preparing a polymer gel according to a third aspect of the present disclosure includes (α) obtaining a first network structure by polymerizing and crosslinking a first monomer component; and (β) obtaining a second network structure entangled with the first network structure by polymerizing and crosslinking a second monomer component in a gel including the first network structure, a solvent, and the second monomer component, the first network structure and the second network structure being entangled with each other to form a polymeric three-dimensional network structure holding the solvent, wherein Step (β) is carried out in a state in which at least a portion of the solvent is crystallized, and a solvent holding pore that holds the solvent even when mechanical energy is applied is formed by Steps (α) and (β), and a solvent exuding pore that actively exudes the solvent when mechanical energy is applied is formed by Step (β).

According to a forth aspect of the present disclosure, provided is an ultrasonic diagnostic probe including the polymer gel according to example embodiments of the present disclosure.

Advantageous Effects of the Invention

According to the present disclosure, achieved are excellent effects of providing a gel having high mechanical strength and an ability to maintain surface wetness for a long time, and a method of preparing the same.

REFERENCE NUMERALS

Figure 1:
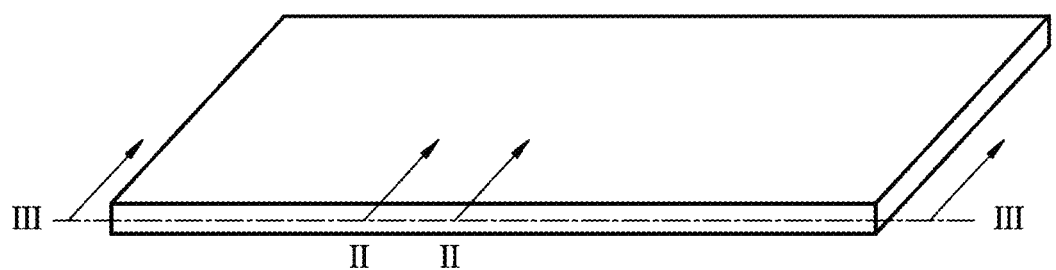
FIG. 1 is a schematic perspective view of a gel according to an embodiment.

1 - - - Gel
2 - - - Three-dimensional network structure
3 - - - Solvent
21 - - - Solvent holding pore
22 - - - Solvent exuding pore
30 - - - Paper towel

BEST MODE

An example embodiment of a polymer gel according to a first aspect of the present disclosure may include a polymeric three-dimensional network structure holding a solvent, and have a solvent exudation property, whereby the solvent included in the gel actively exudes to wet the surface of the polymer gel when mechanical energy is applied thereto.

Work required to elongate the polymer gel may be 3000 J/m$^3$ or more, as measured in a state in which the polymer gel including the solvent has been swelled until equilibrium.

With regard to the gel according to the present disclosure, since the surface wetness may be restored by applying mechanical energy to the gel even if the surface of the gel has dried, applications of the gel to new fields may be expected, starting from fields to which application is limited due to surface drying. In addition, a process of newly adding a solvent or immersing the gel in a solvent so that the solvent is injected into the gel is not excluded, but the solvent in the gel itself may actively exude during use of the gel, and thus, convenience of use thereof is remarkably increased and it is expected to apply the gel in a wide variety of fields. Further, the gel has high mechanical strength, and may therefore be preferably used in all fields requiring wetness. Furthermore, due to its high mechanical strength, the gel may also be preferably used in applications in which the gel is to be placed on a machine, etc., or friction or a force is applied to the gel.

The three-dimensional network structure includes a solvent exuding pore that actively exudes the solvent when mechanical energy is applied thereto, and a solvent holding pore that holds the solvent.

This constitution allows the gel to exhibit a remarkable effect of having both of an excellent solvent exudation property and an excellent solvent holding property.

The polymer gel may be a hydrogel.

When the polymer gel is a hydrogel, its applications may be easily and inexpensively extended to a wide variety of fields.

Further, since various polymer chains are applicable, the gel has an advantage in that it may be easily prepared according to a purpose.

The mechanical energy may be at least one of a compressive force and an ultrasonic wave.

When at least one of a compressive force and an ultrasonic wave is used as the mechanical energy, wetness of the surface may be restored easily.

The three-dimensional network structure may be an interpenetrating network structure including a plurality of network structures in which other polymer chains wind around a network structure serving as a base.

This constitution allows the network structure serving as a base to be flexibly supported by other network structures, thereby obtaining a gel having excellent mechanical properties.

An example embodiment of a method of preparing the gel includes Process A of preparing the polymer gel including a solvent and a polymeric three-dimensional network structure holding the solvent, wherein hydrogen bonding functional groups are included in the three-dimensional network structure or between the three-dimensional network structures; and Process B of freezing the gel to solidify at least a portion of the solvent. A solvent holding pore that holds the solvent even when mechanical energy is applied thereto may be formed mainly by Process A, and a solvent exuding pore that actively exudes the solvent when mechanical energy is applied thereto may be formed by Process B.

Another example embodiment of a method of preparing the gel includes Process α of obtaining a first network structure by polymerizing and crosslinking a first monomer component; and Process β of obtaining a second network structure from a gel including the first network structure, a solvent, and a second monomer component, so that a polymeric three-dimensional network structure holding the solvent may be constructed, in which the second network structure is entangled with the first network structure. Process β may be carried out in a state where at least a portion of the solvent is crystallized, and a solvent holding pore that holds the solvent even when mechanical energy is applied thereto may be formed by Processes α and β, and a solvent exuding pore that actively exudes the solvent when mechanical energy is applied thereto may be formed by Process β.

According to the method of preparing the gel of the above example embodiments, wetness of the surface of the gel may be easily restored.

In the example embodiments of the method of preparing the gel, water may be included as the solvent, and water may form ice crystals in Process β.

In this case, a hydrogel may be readily prepared.

In the example embodiments of the method of preparing the gel, the mechanical energy may be at least one of a compressive force and an ultrasonic wave.

In the example embodiments of the method of preparing the gel, the three-dimensional network structure may be an interpenetrating network structure including a plurality of network structures in which polymer chains wind around a network structure serving as a base.

According to another aspect of the present disclosure, provided is a dry gel. An example embodiment of the dry gel may include no solvent or a solvent in an amount of 80% by weight or less, with respect to 100% by weight of the maximum solvent content in the gel. As the solvent is sufficiently included into the dry gel, the polymer gel having a solvent exudation property of the present disclosure may be formed.

In the present disclosure, the dry gel refers to a gel including (i) no solvent or (ii) a solvent in an amount of 80% by weight or less, with respect to 100% by weight of the maximum solvent content in the gel, as specified above. The dry gel according to the present disclosure may be left in the (i) or (ii) state immediately before use. Therefore, the dry gel is preferred in terms of storage or shipping thereof. Since the gel of the present disclosure may actively exude the solvent included therein to wet the surface thereof when mechanical energy is applied thereto, the gel may be preferably used, for example, in a medical field in which the gel incorporates a drug-containing solvent immediately before use, and is attached to an affected part. Further, while the solvent included in the gel is actively exuded through application of mechanical energy to the gel, the exudative solvent will eventually become depleted, but a new solvent may be added to, and absorbed by the gel, and the gel may be regenerated. Further, the gel including no solvent is a gel including substantially no solvent, and a solvent which is inevitably included is not considered.

The gel of the present disclosure may include a polymeric three-dimensional network structure holding a solvent. The three-dimensional network structure means that polymer chains are branched to a high degree and form a network three-dimensionally. The three-dimensional network structure may be obtained by, for example, polymerizing polymerizable monomers using a crosslinking agent having several polymerizable functional groups. Alternatively, the network structure may be obtained by reacting polymer functional groups with a crosslinking agent or by crosslinking photoreactive groups introduced into side chains by photoradiation.

The polymeric three-dimensional network structure may be exemplified by a network structure composed of a single polymer or a network structure formed by interpenetration of two or more kinds of polymers. When the network structure is used in which a plurality of polymers interpenetrate, each of the polymer chains need not be the network structure, but together, they should form the network structure. Also, the network structure may have a crosslinking structure between polymer chains. So that a strong gel may be provided, it is preferable that the network structure is the interpenetrating network structure including a plurality of network structures in which polymer chains wind around a network structure serving as a base. In view of gel strength and simplification of the preparation process, a double-network type gel is preferable.

The double-network type gel may be exemplified by the disclosure of Patent Document 1. Further, a first crosslinkable polymer constituting a basic skeleton of the gel is formed as a rigid network structure in which hollow parts which are very loose spaces of the network are sporadically distributed, whereas a second non-crosslinkable polymer having a random coil shape is concentrated in the hollow parts to maintain flexibility, and physically winds around the network structure of the first polymer at its ends. Here, ["physically winds around]" means that two or more non-continuous line-shaped objects are not bonded with each other via covalent bonds, etc., but have a positional relationship in which their spatial positions may be constrained by each other, and the wound objects become disengaged from each other when one or both of them are physically destroyed or deformed.

The solvent held in the gel of the present disclosure is not particularly limited, as long as it is impregnated and held in the three-dimensional network structure, and a single solvent or multiple kinds of solvents may be used. For example, the solvent may be a hydrophilic solvent such as water, or an alcohol, for example, ethanol, isopropyl alcohol, 3-methoxy-3-methyl-1-butanol, etc.; glycols such as propylene glycol, ethylene glycol, etc.; glycol esters such as ethylene glycol monoethylether, etc., dimethyl sulfoxide, tetrahydrofuran, cyclohexane, etc.

Arbitrary materials may be dissolved or dispersed in the solvent. For example, a solvent, to which a cosmetic ingredient such as hyaluronic acid, etc., a surfactant, a drug, etc. is arbitrarily added, may be preferably used as the solvent. In terms of handling and safety, a hydrogel using water as the solvent is preferred. Further, a small amount of a hydrophilic solvent such as alcohol, etc. may be preferably added to the water. In the present disclosure, the solvent is included in the category of [hydrogel] when 20% or more by volume of the solvent is water.

The gel of the present disclosure has a solvent exudation property by which the surface of the gel is wetted due to the solvent included therein being actively exuded when mechanical energy is applied thereto. Here, the mechanical energy may include mechanical stress, for example, a tensile force, a compressive force, a twisting force, a bending force, a shearing force, etc. Further, the mechanical energy may be exemplified by ultrasonic waves, shockwaves, etc. Further, the mechanical energy may correspond to a surface tension of the gel, resulting in a capillary phenomenon such as that which occurs by contact with paper, etc. Preferred examples may vary depending on a purpose of use, but at least one of compressive force and ultrasonic waves is preferred in terms of convenience, etc. Further, the level of mechanical energy in the present disclosure may be sufficient to deform the three-dimensional network structure, but does not result in destruction of the three-dimensional network structure.

Further, the included solvent refers to a solvent included in the gel, and includes not only the solvent on the surface of the gel but also the solvent included therein. Further, ["solvent exudation property]" means that the surface of the gel becomes wet by applying the mechanical energy thereto. The solvent exudation property means that the surface of the gel of the present disclosure is provided with wetness by applying the mechanical energy to the gel, without destruction of the polymeric three-dimensional network structure and addition of any solvent from the outside. That is, by applying the mechanical energy to the gel, the solvent that is not restrained by the polymer constituting the network of the gel may be transferred to the surface of the gel. Further, addition of a solvent from the outside is not excluded.

A form of the gel is not particularly limited, and the gel may have any form. For example, the gel may be in a sheet or plate form, or in spherical, rectangular parallelepiped, or bead form, depending on a purpose of use. Further, any combination of the forms may be used or a plurality of gels may be used repeatedly. In terms of toughness, a thickness of the gel is preferably 1 mm or more, more preferably 2 mm or more, and most preferably 3 mm or more.

Figure 2:
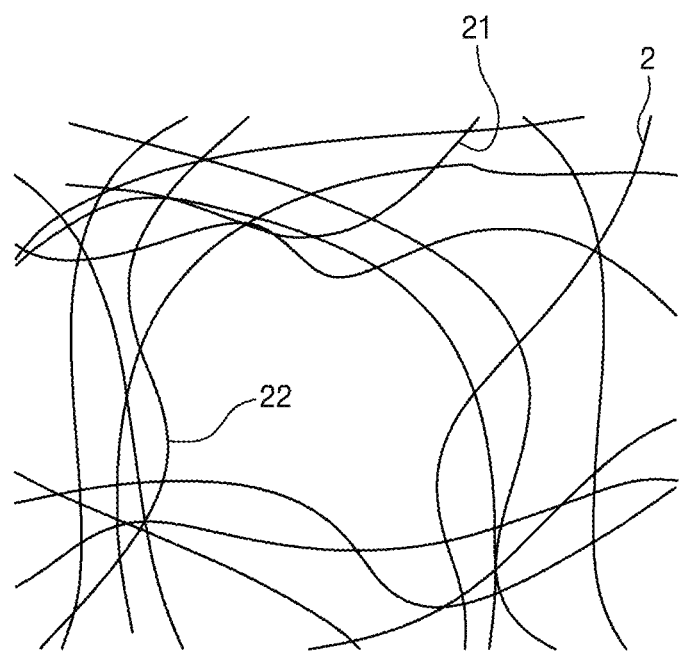
FIG. 2 is a enlarged partial cross-sectional view of a three-dimensional network structure only, taken along line II-II of FIG. 1.

A schematic perspective view of an example gel according to the present embodiment is shown in FIG. 1, and an enlarged partial cross-sectional view of a three-dimensional network structure only, taken along line II-II of FIG. 1, is shown in FIG. 2. A gel 1 has a sheet form. A thickness of the sheet is not particularly limited, but with respect to toughness, is preferably 1 mm or more. The gel 1 has a polymeric three-dimensional network structure 2 therein, as illustrated in FIG. 2. The polymeric three-dimensional network structure 2 has at least a small solvent holding pore 21 and a large solvent exuding pore 22. Sizes or ratios of the solvent holding pore 21 and the solvent exuding pore 22 may be designed in consideration of mechanical energy to be applied, etc. In an initial gel in a state in which it is swelled to an equilibrium, a solvent is included in the solvent holding pore 21 and the solvent exuding pore 22.

The gel (initial gel) of the present embodiment may be elongated with work of 3000 $J/m^3$ or more, as measured in a state in which it is swelled to equilibrium. As the energy applied until a material is destroyed is determined as 3000 $J/m^3$ or more, a gel having high toughness and superior durability may be provided, and when the mechanical energy is applied to the gel, it may not be destroyed within a sufficiently wide energy range. Further, in addition to a field in which surface wetness is required, the gel may be preferably applied to fields involving friction or requiring a sliding property. Work required for elongation is preferably 4000 $J/m^3$ or more, and particularly preferably 5000 $J/m^3$ or more. In the present disclosure, the value of breaking toughness refers to a value obtained by measuring in Examples described below.

In order to increase toughness, it is effective to have a mechanism (sacrificial bond) for dissipating energy before the whole gel is broken. The sacrificial bond may include, for example, covalent bonds, ionic bonds, hydrogen bonds, complexes, hydrophobic interactions, and van der Waals forces. The sacrificial bond may be preferably obtained by using a double-network gel having the above-described double-network structure. By using the double-network structure, one of the networks thereof may be effectively broken inside when the whole gel is deformed, but before the whole gel is broken, so that the energy required for breaking the whole gel may be greatly increased.

Figure 3:
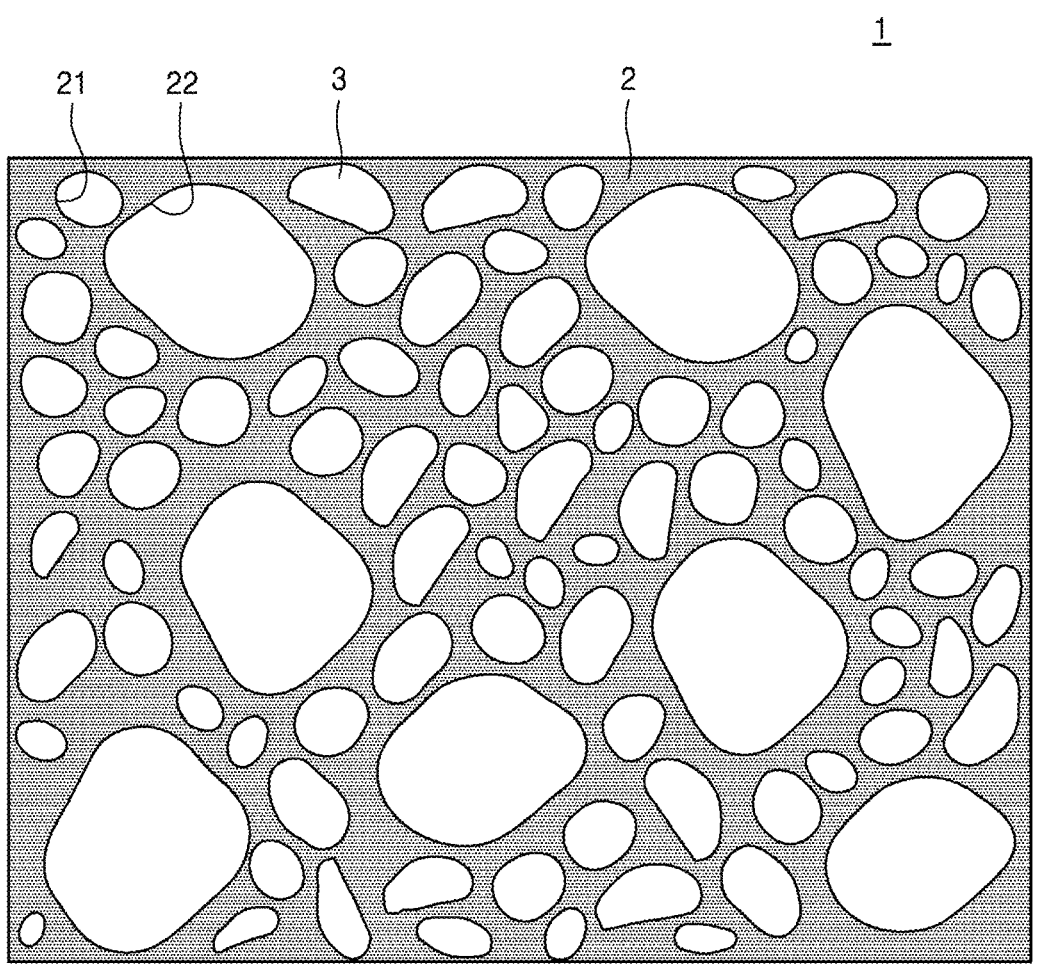
FIG. 3 is a cross-sectional view schematically illustrating an example arrangement of a solvent and a three-dimensional network structure, taken along line III-III of FIG. 1.

FIG. 3 shows a cross-sectional view, taken along line III-III of FIG. 1, schematically illustrating an example arrangement of a solvent and a three-dimensional network structure. A solvent 3 is, as illustrated in FIG. 3, included in the solvent holding pore 21 and the solvent exuding pore 22. The solvent holding pore 21 plays a role in holding the solvent 3 in the gel 1 even when external mechanical energy is applied thereto, and the solvent exuding pore 22 plays a role in exuding the included solvent to the gel surface when external mechanical energy is applied. Depending on a shape or size of the solvent exuding pore 22, a solvent exudation rate or an amount of the mechanical energy required for exudation of the solvent may vary, and therefore, a plurality of solvent exuding pores 22 having different sizes and shapes may be arranged in the gel, and the amount of the solvent remaining in the gel may be controlled to obtain an appropriate exudation amount.

From the viewpoint of maintaining the shape of the solvent holding pore 21 and the solvent exuding pore 22, it is preferable that the shape of the three-dimensional network structure is memorized and the structure thereof is maintained. Therefore, the structures of the solvent holding pore 21 and the solvent exuding pore 22 may be further strengthened to provide a strong gel. A method of memorizing the shape of the three-dimensional network structure may be exemplified by a method of constructing the shape by a polymerization process and a method of changing the pore size by a process of freeze-drying the obtained gel and memorizing the shape via hydrogen bonds. In particular, when water is used as the solvent, a solvent holding property of the solvent holding pore 21 may be further enhanced, and durability of the three-dimensional network structure itself may be enhanced by the hydrogen bonding of the three-dimensional network structure. Accordingly, an advantage is provided in that respective functions of the solvent holding pore 21 and the solvent exuding pore 22 may be more effectively improved.

Figure 4:
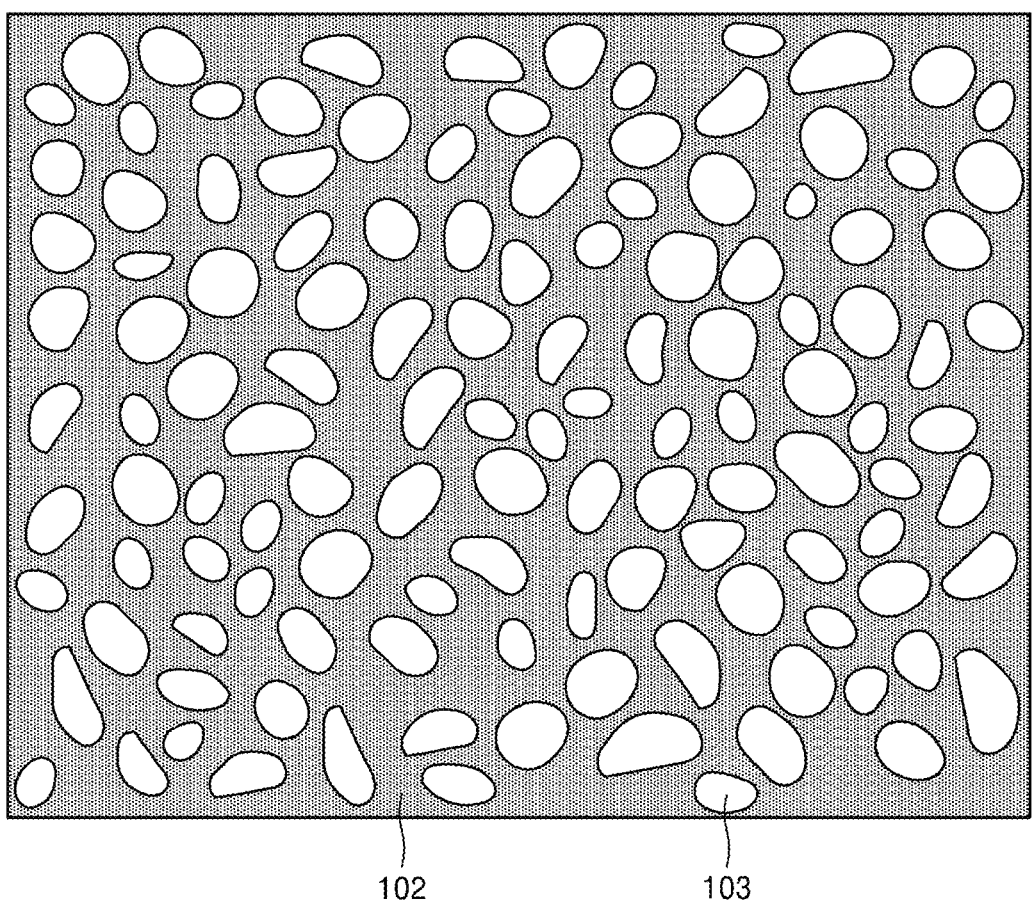
FIG. 4 is a cross-sectional view schematically illustrating an example arrangement of a solvent and a three-dimensional network structure of a gel according to a conventional example, corresponding to the positions in the cross-sectional view taken along line III-III.
Figure 5:
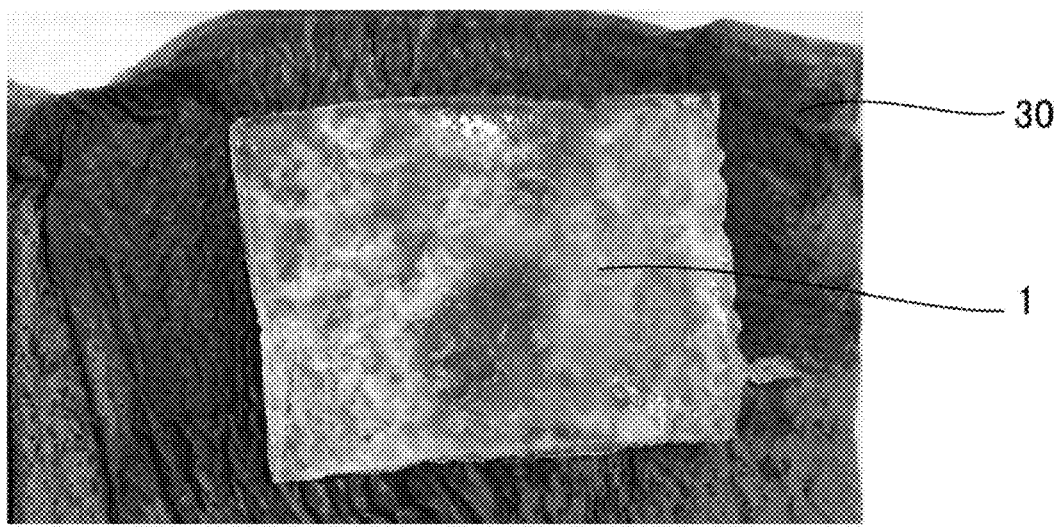
FIG. 5 is a photograph showing water exudation properties when a gel according to Example 2 was placed on a paper towel (Kim towel).

FIG. 4 shows a schematic illustration of an example arrangement of a solvent and a three-dimensional network structure of a gel, according to a conventional example, corresponding to the positions in a cross-sectional view taken along line III-III of FIG. 1. In the conventional example, as illustrated in FIG. 4, a number of small pores corresponding to the solvent holding pore 21 are provided, and therefore, a solvent 103 is held in a gel 101. Since the gel 101 according to the conventional example has a three-dimensional network structure 102 in which polymer chains are very intricately interconnected, and the solvent molecules may not move easily, the solvent, for example, water, may be trapped at a high ratio inside the gel. However, a problem exists in that the surface of the gel dries over time and the wettability thereof deteriorates. In the conventional gel, even if a compressive force is applied, the solvent hardly exudes to the gel surface. Even though a portion of the solvent exudes, a diffusion rate of the molecules of the solvent is extremely low, and only a very small amount of the solvent exudes, such that wetness may not be imparted to the surface with a force that does not destroy the gel.

On the other hand, in the gel of the present embodiment, when a compressive force is applied to the gel 1, the solvent actively exudes from the solvent exuding pores 22 to the gel surface, providing wetness to the surface. According to the gel of the present disclosure, a portion of the solvent included in the solvent exuding pores 22 exudes to the surface through application of mechanical energy. By applying mechanical energy of a condition resulting in solvent exudation, it is possible to repeatedly provide wetness to the surface.

By repeated use, the solvent included in the solvent exuding pore 22 eventually becomes depleted. However, since the gel has the three-dimensional network structure and also has the solvent holding pore 21, its function as a gel may be maintained. The surface wetness may be prolonged by controlling a size and a ratio of the solvent exuding pore 22 or intensity of mechanical energy.

The gel 1 may be disposable, but may be regenerated by adding the solvent again into the gel.

An optimum strength of the compressive force may be within a range in which the three-dimensional network structure is not destroyed and wetness of the surface is obtained. Although it is dependent on the constitution of the gel, a pore size of the solvent holding pore 21 is preferably 500 nm or less, more preferably 200 nm or less, and much more preferably 100 nm or less, with respect to a flow rate per unit time. A lower limit of the pore size of the solvent holding pore (21) is not particularly limited as long as it may hold the solvent.

Further, the solvent exuding pore 22 preferably has a pore size of 3 mm or less, more preferably 1 mm or less, and most preferably 0.5 mm or less, with respect to holding the solvent under non-stimulation. With respect to a flow rate per unit time, the pore size of the solvent exuding pore 22 is preferably 0.5 µm or more, more preferably 1 µm or more, and much more preferably 2 µm or more.

The gel of the present disclosure preferably has a solvent content of 10% or more (more preferably 50% or more, and much more preferably 85% or more). As described above, the presence of a large amount of solvent in the gel improves ductility and permeability of a substance, which is useful in a drug delivery system (DDS) or in applications requiring sustained release. An upper limit of the solvent content is not particularly limited, but is generally 99.9% or less, preferably 99% or less, and more preferably 95% or less, with respect to maintaining the mechanical strength of the gel. In addition, the gel of the present disclosure preferably has shrinkage of 20% to 95% (more preferably 60% to 95%, and most preferably 70% to 95%).

An optimum range of a compressive failure stress of the gel may vary depending on an application thereof, but is preferably 1 MPa to 100 MPa, more preferably 5 MPa to 50 MPa, and most preferably 10 MPa to 40 MPa.

Further, an optimum range of the tensile failure stress of the gel may vary depending on an application thereof, but is preferably 0.1 MPa to 100 MPa, more preferably 0.1 MPa to 50 MPa, and most preferably 0.5 MPa to 5 MPa.

The solvent exudation property increases, as the pore size of the solvent exuding pore 22 increases and the number of the solvent exuding pore 22 increases, and therefore, the gel may be prepared in consideration of the solvent exudation property depending on the applications.

The dry gel of the present disclosure includes no solvent or 80% by weight or less of the solvent with respect to 100% by weight of the maximum solvent content that may be included in the gel. Further, the above-described gel may be prepared by including a sufficient amount of the solvent. The gel of the present disclosure may be advantageous in terms of storage and shipping thereof since the solvent may be included in the gel immediately before use. In addition, the gel of the present disclosure may absorb a solvent which is newly added, and therefore, it may be possible to recycle the gel.

Subsequently, one embodiment of the method of preparing the gel according to the present disclosure will be described. However, the method of preparing the gel of the present disclosure is not limited to the following methods.

[Preparation Method 1]

First, a gel having a polymeric three-dimensional network structure holding a solvent is prepared (Process A). The obtained gel is frozen to solidify the molecules of the solvent in a dispersed state (Process B). A solvent holding pore 21 that holds the solvent even when mechanical energy is applied thereto is formed mainly by Process A. Further, a solvent exuding pore that actively exudes the solvent when mechanical energy is applied thereto is formed by Process B.

Process A may be carried out by a conventional known method of preparing the gel. Here, a hydrogel having an interpenetrating three-dimensional network structure will be described as an example.

First, a first monomer component, which is an unsaturated monomer of which 10 mol % or more is charged, is polymerized and crosslinked. In detail, a crosslinking agent is added to the first monomer component, if necessary, and an additive such as a polymerization initiator, etc. is added to carry out a polymerization reaction. As a result, a first network structure is formed. Subsequently, an additive such as a polymerization initiator, etc. is added to a second monomer component, which is an unsaturated monomer of which 60 mol % or more is electrically neutral, and if necessary, a crosslinking agent is added thereto, thereby a second monomer solution being prepared. In this solution, the gel having the first network structure is immersed, and the second monomer component, the initiator, etc. are sufficiently dispersed in the gel for a sufficient time. The gel is then removed from the solution to polymerize the second monomer component in the gel. Through this process, a hydrogel of a double-network structure is obtained, in which a second network structure is formed in the first network structure (see FIG. 1). As the gel is prepared as the double-network structure, the first network structure may be supported by the second network structure with flexibility, thereby enhancing strength of the gel. In the same manner, hydrogels of a triple or greater-network structure may also be prepared.

Here, when crosslinking is carried out by adding the second monomer component to the polymerization, it is preferable to set the degree of crosslinking to be smaller than that in the case of carrying out crosslinking by polymerizing the first monomer component. The degree of crosslinking may be easily adjusted by controlling the amount of the crosslinking agent. Preferably, the first network structure has a degree of crosslinking of 0.1 mol % to 50 mol %, and the second network structure has a degree of crosslinking of 0.001 mol % to 20 mol %. More preferably, the first network structure has a degree of crosslinking of 1 mol % to 20 mol %, and the second network structure has a degree of crosslinking of 0.01 mol % to 5 mol %. Most preferably, the first network structure has a degree of crosslinking of 2 mol % to 10 mol %, and the second network structure has a degree of crosslinking of 0.05 mol % to 1 mol %. Particularly, in order to increase the solvent content of the gel (that is, to increase a swelling degree), it is preferable that the degree of crosslinking of both network structures is decreased, and in order to increase the modulus of elasticity, it is preferable that the degree of crosslinking of both network structures is increased.

The gel may be a gel having a plurality of network structures, in which the second network structure uniformly winds around the first network structure serving as a base, or a gel having a plurality of network structures, in which the linear polymer uniformly winds around the first network structure serving as a base. A molar ratio of the amount of the first monomer component:the amount of the second monomer component in the hydrogel is preferably 1:2 to 1:100 (preferably 1:3 to 1:50, more preferably 1:3 to 1:30), with respect to providing properties such as mechanical strength, etc.

Here, the unsaturated monomer having a charge may be preferably an unsaturated monomer having an acidic group (e.g., a carboxyl group, a phosphoric acid group, or a sulfonic acid group) or an alkaline group (e.g., an amino group), for example, 2-acrylamide-2-methyl propane sulfonic acid, acrylic acid, methacrylic acid, or salts thereof. Further, the electrically neutral unsaturated monomer may include, for example, acrylamide, N-isopropylacrylamide, vinyl pyridine, styrene, methyl methacrylate, a fluorine-containing unsaturated monomer (e.g., trifluoroethyl acrylate), hydroxyethyl acrylate, or vinyl acetate. The amount of the unsaturated monomer having a charge in the first monomer component is 10 mol % or more, but preferably 100 mol %, with respect to the first monomer component. In addition, the amount of the unsaturated monomer having no charge in the second monomer component is 10 mol % or more, but preferably 100 mol %, with respect to the second monomer component.

The hydrogen bond may be easily obtained by polymerizing a copolymer, the copolymer including a monomer as a proton acceptor and a monomer as a proton donor, to obtain a polymer. Examples of the monomer as the proton acceptor may include 2-ureide ethyl (meth)acrylate and 2-ureide methyl (meth)acrylate. Examples of the monomer as the proton donor may include monomers having a carboxyl group, such as (meth)acrylic acid.

Also, when each network structure is composed of one kind of monomer, the amount of the monomer in the gel is determined by elemental analysis. Further, in the case of using two or more kinds of monomers, elemental analysis is complicated, and in some cases, the amount of the monomers may not be determined. In this case, for example, the amount of the monomer may be obtained by subtracting the amount of the monomer not polymerized from the amount of the monomer used in the preparation.

The first monomer component preferably includes 10 mol % or more of the unsaturated monomer having a charge. For example, the electrically neutral unsaturated monomer which is essentially used as the second monomer component may be used. The second monomer component is not particularly limited, as long as it includes 60 mole % or more of an electrically neutral unsaturated monomer. For example, the unsaturated monomer having a charge essentially used as the first monomer component may be used. For example, 2-acrylamide-2-methylpropanesulfonic acid (AMPS), acrylamide (AAm), acrylic acid (AA), methacrylic acid, N-isopropyl acrylamide, vinyl pyridine, hydroxyethyl acrylate, vinyl acetate, dimethyl siloxane, styrene (St), methyl methacrylate (MMA), trifluoroethyl acrylate (TFE), etc. may be used. Further, a polysaccharide such as gellan, hyaluronic acid, carrageenan, chitin, alginic acid, etc., or a protein such as gelatin, collagen, etc. may be used.

With respect to improving mechanical strength, it is preferable to use both a water-insoluble monomer and a water-soluble monomer as organic monomer raw materials. In this regard, the water-insoluble monomer may be used only for the first network structure, or used only for the second network structure or the linear polymer, or used for both of them. A ratio of the water-insoluble monomer:the water-soluble monomer is preferably 9.9:0.1 to 0.1:9.9. In the first network structure, a ratio of the water-soluble monomer:the water-insoluble monomer is more preferably 0:100 to 1:99, and in the second network structure or the linear polymer, a ratio of the water-soluble monomer:the water-insoluble monomer is more preferably 0:100 to 1:99. Further, in the first network structure, a ratio of the water-soluble monomer:the water-insoluble monomer is more preferably 0:100 to 1:99, and in the second network structure, a ratio of the water-soluble monomer:the water-insoluble monomer is more preferably 0:100 to 5:95. In order to decrease a water content of the gel, a content of hydrophobic monomers may be increased.

The water-insoluble monomer may include, for example, fluorine-containing monomers, such as 2,2,2-trifluoroethyl-methyl acrylate, 2,2,3,3,3-pentafluoropropyl methacrylate, 3-(perfluorobutyl)-2-hydroxypropyl methacrylate, 1H,1H, 9H-hexadecafluorononyl methacrylate, 2,2,2-trifluoroethyl acrylate, 2,3,4,5,6-pentafluorostyrene, vinylidene fluoride, etc.

It is also preferable to form a complex in the gel by using a monomer having a group capable of forming the complex with a metal ion as an organic monomer raw material and by introducing the metal ion into the gel. In general, when a complex formation ratio in the gel, that is, a metal introduction ratio, is increased, the solvent content may be reduced and the mechanical strength may be increased. In this regard, the monomer having a group capable of forming a complex with a metal ion may be used only for the first network structure, or used only for the second network structure (interpenetrating network structure hydrogel) or linear polymer (semi-interpenetrating network structure hydrogel), or used for both of them. It is preferable that a complex with a metal ion is formed in the first network structure. Further, a metal content is preferably 0.03 mol/L to 1 mol/L, and more preferably 0.01 mol/L to 0.3 mol/L. A content of the monomer having a group capable of forming a complex is preferably 10 mol % to 100 mol %, and more preferably 30 mol % to 100 mol %, with respect to the total amount of the monomers constituting the first network structure.

A ratio of the metal ion and the monomer having a group capable of forming a complex is preferably 1:1 to 1:1000, and more preferably 1:10 to 1:100. The metal ion is not particularly limited as long as it is a metal ion capable of forming a complex, and examples thereof may include a zinc ion, an iron ion, a nickel ion, a cobalt ion, a chromium ion, etc. The group capable of forming a complex with a metal ion refers to a group capable of forming a complex with the selected metal ion. For example, when a polyvalent metal such as zinc, iron, nickel, cobalt, chromium, etc. is selected as the metal ion, a carboxyl group, a sulfonic acid group, or a phosphoric acid group may be exemplified. Examples of the monomer containing a group capable of forming a complex with a metal ion may include acrylic acid, methacrylic acid, itaconic acid, styrene sulfonic acid, vinyl phosphoric acid, etc.

The polymerization initiator is not particularly limited, and is selected from a variety of polymerization initiators depending on the organic monomers to be polymerized. For example, when AMPS, AAm, or AA as an organic monomer is thermally polymerized, a water-soluble thermal catalyst such as potassium persulfate, etc. or a redox initiator such as potassium persulfate-sodium thiosulfate, etc. may be used, and, in the case of photopolymerization, 2-oxoglutaric acid may be used as a photosensitizer. Further, when St as an organic monomer is thermally polymerized, a soluble thermal catalyst in an organic solvent such as azobisisobutyronitrile (AIBN), benzoyl peroxide (BPO), etc. may be used, and, in the case of photopolymerization, benzophenone may be used as a photosensitizer.

Further, the crosslinking agent is not particularly limited, and is selected from a variety of crosslinking agents depending on the organic monomer to be crosslinked and polymerized. For example, when AMPS, AAm, or AA is used as the organic monomer, N,N'-methylenebisacrylamide may be used. When St is used as the organic monomer, ethylene glycol dimethacrylate may be used. In addition, with respect to a solvent of a solution for immersing the gel having the first network structure, the solvent of the solution is preferably the same as the solvent in the gel having the first network structure, so that adverse effects on the gel to be immersed in the solution may be prevented and desirable winding of the double-network structure or linear polymer around the network of the first network structure may be achieved. Further, with respect to the solvent finally included in the gel, the solvent may be used from the preparation step, or the solvent may be exchanged after the preparation. In the case of the metal ion being introduced into the gel, the obtained interpenetrating network structure hydrogel is dried under vacuum, and then immersed in a solution of the metal salt. According to this manipulation, the distance between the networks may be reduced to the smallest distance, thereby efficiently forming a complex with the metal ion.

A polymerization reaction of the second monomer component diffused to the gel having the first network structure may be carried out by a method of cooling, heating, and/or irradiating active rays such as UV rays, etc. This polymerization reaction is carried out under conditions that do not impair the first network structure of the gel. The crosslinking reaction is carried out by mixing a predetermined concentration of the crosslinking agent and the reaction initiator together with the second monomer component in the solvent and diffusing this mixture into the gel having the first network structure. Specifically, the gel having the first network structure is immersed in the second monomer solution containing the crosslinking agent, and, the second monomer solution is allowed to diffuse into the the gel having the first network structure, for example, at a low temperature for 24 hours. Also, in order to prevent crosslinking during diffusion, the low temperature is preferably room temperature or lower, for example, around 4° C.

In Process B, at least a portion of the solvent impregnated in the gel is frozen for solidification. A ratio of the solvent exuding pore 22 to the solvent holding pore 21, and a size of the solvent exuding pore 22, may be designed depending on an application in which an exudation property is to be provided. They may be controlled by adjusting the time and freezing temperature. If the size of the solvent exuding pore 22 is to be increased, the freezing temperature may be lowered, and/or the freezing time may be increased. By Process B, the solvent exuding pore 22 shown in FIG. 3 may be formed. The size of the solvent exuding pore 22 need not be uniform and may be non-uniform.

In the case of hydrogel, the freezing is carried out at 0° C. or lower with respect to ice crystallization. In terms of the freezing point drop, the temperature is preferably −5° C. or lower, and more preferably −10° C. or lower. Further, the freezing time is preferably 1 minute or longer with respect to ice crystal growth. To obtain an effect of larger crystal growth, the freezing time is more preferably 5 minutes or longer. Further, with respect to progression of the polymerization reaction, the freezing time is preferably 120 minutes or less. The hydrogel preferably has a thickness of 0.1 mm to 10 mm so that the temperature throughout the gel is uniform upon performing the freezing process.

In order to control the solvent exudation property, the solvent exuding pore may be designed to have a different size in the thickness direction. For example, a member satisfying the freezing condition may be approached to a main surface side to be provided with the surface exudation property, and the solvent exuding pore 22 may be designed to exist in a relatively large number on the main surface side. Further, if slow solvent exudation is desired, the solvent exuding pore 22 may be designed so that the size thereof increases by taking the member away, in the thickness direction, from the main surface side to be provided with the surface exudation property.

According to Preparation Method 1, since the solvent exuding pore is prepared by freezing after the preparation of the gel, an advantage is provided in that the preparation process is simple. It is also preferable that, after freezing, the solvent exuding pore is retained by hydrogen bonding, and after thawing, a microstructure may be more effectively maintained by hydrogen bonding.

[Preparation Method 2]

Next, an example of a preparation method different from the above preparation method will be described. In Preparation Method 2, a first network structure is first obtained by polymerizing and cross-linking the first monomer component (Process α). Subsequently, in order to construct a polymeric three-dimensional network structure (for holding a solvent) which interconnects with the obtained first network structure, a second network structure is obtained from a gel including the first network structure, a solvent, and a second monomer component (Process β). A process using water as the solvent will be described.

Process β is carried out while at least a portion of the solvent is crystallized. By Process α and Process β, a solvent holding pore that holds the solvent even when mechanical energy is applied thereto is formed, and a solvent exuding pore that actively exudes the solvent when the mechanical energy is applied thereto is formed by the process β. Here, a hydrogel having an interpenetrating three-dimensional network structure will be described as an example.

Process α is carried out to obtain the first network structure in the same manner as in Preparation Method 1. For example, an aqueous solution including an unsaturated monomer having a charge, an electrically neutral unsaturated monomer, as needed, a crosslinking agent, and an additive such as a UV radical polymerization initiator is prepared, and the aqueous solution is irradiated with UV rays to obtain the first network structure.

Subsequently, the gel obtained in Process α is swollen in a sufficient amount of the aqueous solution containing the second monomer component. The swollen gel is cooled in each immersion liquid. A cooling temperature used is a temperature at which crystals of water as the solvent are obtained. Then, two sheets of glass, of which the main surface is coated with a radical generating agent, are prepared. After cooling sufficiently, the above-described swollen gel is interposed between the pair of glass sheets, and polymerized at a temperature at which ice crystals are formed to form a second network structure. A polymerization time is defined as a time taken to sufficiently polymerize the second monomer component. By polymerizing under the condition in which the solvent is frozen, the gel is not formed in a region where the solvent is frozen. That is, the gel is formed in the unfrozen region. As a result, a porous gel is obtained. The monomer-concentrated region is polymerized under non-freezing conditions. That is, a gel such as a sponge having holes with a solvent exudation property is formed in the region where solvent crystals are present. After polymerization, the gel is thawed at room temperature, added into pure water, and washed with the pure water several times to remove unreacted raw materials, etc. A hydrogel is obtained through this process.

The monomers described in Preparation Method 1 may be used, for example, as the preferable monomer component. When crosslinking is carried out by adding the second monomer component to the polymerization, it is preferable to set the degree of crosslinking to be smaller than that in the case of carrying out crosslinking by polymerizing the first monomer component. The preferred range of the degree of crosslinking is as described in Preparation Method 1. A ratio of the amount of the first monomer component:the amount of the second monomer component is preferably within the range as described in Preparation Method 1, with respect to imparting mechanical strength, etc. The first monomer component preferably includes 10 mol % or more of the unsaturated monomer having a charge.

In terms of improving the mechanical strength, it is preferable to use both a water-insoluble monomer and a water-soluble monomer as the organic monomer raw material. In this regard, the water-insoluble monomer may be used only for the first network structure, used only for the second network structure or the linear polymer, or used for both of them. The preferred ratio is the same as in Preparation Method 1. Further, in Preparation Method 2, a monomer having a group capable of forming a complex with a metal ion may be used to receive the metal ion.

Further, the compounds listed in Preparation Method 1 may serve as examples of a polymerization initiator and a cross-linking agent.

In the case of hydrogel, Process β is carried out at 0° C. or lower in view of ice crystallization. With respect to the freezing point drop, the temperature is preferably −5° C. or lower, and more preferably −10° C. or lower. To prevent the gel from cracking, freezing and polymerizing are preferably carried out at −50° C. or higher. Further, the freezing time is preferably 1 minute or longer in view of ice crystal growth. To obtain the effect of larger crystal growth, the freezing time is more preferably 5 minutes or longer. Further, With respect to progression of the polymerization reaction, the freezing time is preferably 120 minutes or less. The hydrogel preferably has a thickness of 50 mm or less so that the temperature throughout the gel is uniform upon performing the freezing process.

Particularly, by controlling the kind and amount of the compound of the second monomer component and the amount of the crosslinking agent, the solvent exudation property may be controlled. According to Preparation Method 2, by polymerizing under freezing conditions, the solvent may be purposely solidified and the solvent exuding pores may be easily prepared. Further, since the monomers are polymerized under the freezing conditions, the microstructure may be maintained even after thawing.

Next, a method of preparing a dry gel will be described. The dry gel may be prepared by removing the solvent, through an evaporation process (for example, air drying, heat drying, freeze drying, etc.), from the gel obtained by Preparation method 1 or Preparation method 2. Alternatively, the dry gel may be prepared by immersing the gel obtained by Preparation method 1 or Preparation method 2, into a solvent which is a compatible solvent with the solvent contained within the gel, but a poor solvent for the gel, thereby, removing the contained solvent from the gel obtained by Preparation method 1 or Preparation method 2. Alternatively, the dry gel may be prepared by bulk polymerization without using a solvent upon synthesis.

The gel according to the present disclosure has the solvent exudation property, whereby the included solvent actively exudes to wet the surface of the gel when mechanical energy is applied to the gel. Therefore, applications of the gel to new fields may be expected, starting from fields to which application is limited due to surface drying. For example, the gel is preferably used in a cooling gel sheet, a medical material such as a wet compress for applying a medicine to skin, a cosmetic material such as a face mask, a cell culture medium, and an acoustic coupling gel (e.g., application to an ultrasonic diagnostic probe) (more specifically, the ultrasonic diagnostic probe may include a transducer for generating ultrasonic waves and transmitting and receiving ultrasonic waves, a contact part disposed in front of the transducer to contact a subject, and a medium which is packed between the transducer and the contact part to transmit ultrasonic waves of the transducer to the contact part. In this regard, at least one of the contact part and the medium may include the gel according to the present disclosure). A gel having high mechanical strength is applicable to fields requiring frictional resistance, and is preferably used as a sliding member.

MODE OF THE INVENTION

Examples (Measurement of Breaking Strength)

Toughness may be evaluated by measuring work required for elongation. The work for elongation may be calculated from an area under a stress-strain curve corresponding to when a test specimen was broken by elongation using a tensile tester (Orientec Co., RTC-1150A). The work for elongation was measured in a swelling state reached by swelling raw materials in a solvent until equilibrium. The test specimen is preferably dumbbell-shaped, and the shortest side thereof is preferably at least 10 times the pore size. In the present disclosure, a dumbbell-shaped JISK-6151-7 specimen was used as the test specimen.

Example 1

10.4 g of sodium acrylamide methyl propane sulfonate, 0.31 g of methylene bisacrylamide, and 0.007 g of oxoglutaric acid were dissolved in pure water to prepare 50 mL of an aqueous solution in a 50 mL volumetric flask. This solution was injected into a glass mold of a dimensions of 8 cm×8 cm×2 mm and then irradiated with UV light for 8 hours under an argon atmosphere to synthesize a gel having a first network structure.

The resulting gel was divided into four portions and added to 500 mL of an aqueous solution containing 71.1 g of acrylamide, 0.15 g of methylenebisacrylamide, and 0.15 g of oxoglutaric acid. The gel absorbed this aqueous solution and swelled by about 10 times in volume. The gel was interposed between two sheets of glasses, and irradiated with UV light for 8 hours under an argon atmosphere to synthesize a second network structure. Subsequently, after the synthesis, the gel, which was equilibrated and swollen with pure water, was put into a freezer at −50° C., and a portion of the solvent was solidified. Thereafter, the gel was taken out from the freezer, thawed, and then immersed into pure water to obtain a gel according to Example 1.

Example 2

1.4 g of acrylamide, 6.9 g of sodium acrylamide methyl propane sulfonate, 0.08 g of methylene bisacrylamide, and 0.005 g of oxoglutaric acid were dissolved in pure water to prepare 50 mL of an aqueous solution in a 50 mL volumetric flask. This solution was injected into a glass mold of dimensions of 8 cm×8 cm×2 mm and irradiated with UV light for 8 hours under an argon atmosphere to synthesize a gel having a first network structure.

The resulting gel was divided into six portions and added to 500 mL of an aqueous solution containing 35.5 g of acrylamide, 0.008 g of methylenebisacrylamide, and 0.73 g of ammonium persulfate. The gel absorbed this aqueous solution and swelled by about 10 times in volume.

Subsequently, the swollen gel was cooled in an immersion solution at −5° C. 0.15 mL/sheet of tetramethylethylenediamine was applied to 12 glass sheets which were then cooled at −20° C. When both the gel and the glass reached a predetermined temperature, the gel was interposed between the glass sheets so that an tetramethylethylenediamine-coated surface was in contact with the gel, put in a freezer at −50° C., and left for 24 hours to polymerize a second network structure.

Thereafter, the gel was taken out from the freezer, thawed, and then immersed into pure water. Pure water was replaced three times to remove unreacted raw materials to obtain a gel according to Example 2.

The gel sheet obtained by Example 2 was left on a water-absorbing paper towel (name: Kim towel) for 2 hours, and water was exuded from the gel by surface tension of the paper towel. Water absorption was examined with the naked eye. Further, work for elongation was measured by the above-described method, and as a result, the work for elongation was found to be 9610 J/m$^3$, indicating sufficiently strong breaking strength.

Comparative Example 1

1.5 g of acrylamide, 6.5 g of sodium acrylamide methyl propane sulfonate, 0.1 g of methylene bisacrylamide, and 0.1 g of ammonium persulfate were dissolved in pure water to prepare 50 mL of an aqueous solution in a 50 mL volumetric flask. This aqueous solution was cooled at −5° C., and then 0.3 mL of tetramethylethylenediamine was added thereto, followed by sufficient stirring of the solution. This aqueous solution was injected into a glass mold of dimensions of 8 cm×8 cm×2 mm which had been cooled at −20° C. in advance, and left in a freezer at −50° C. for 24 hours. Thereafter, the gel was taken out from the freezer, thawed, and then poured into pure water. Pure water was replaced three times to remove unreacted raw materials to obtain a gel. Work for elongation of the gel according to Comparative Example 1 was measured by the above-described method, and as a result, the work for elongation was found to be 180 J/m$^3$.

Further, a commercially available gel was placed on a Kim towel, and its absorption was evaluated. Even after being left for 2 hrs, absorption by the Kim towel was not observable with the naked eye.

The invention claimed is:

1. An ultrasonic diagnostic probe comprising:
a transducer configured to transmit and receive ultrasonic waves;
a contact part disposed in front of the transducer, and configured to contact a subject; and
a medium which is disposed between the transducer and the contact part, and configured to transmit the ultrasonic waves of the transducer to the contact part,
wherein the contact part or the medium includes a polymer gel including a polymeric three-dimensional network structure,
the polymeric three-dimensional network structure includes a plurality of solvent holding pores and a plurality of solvent exuding pores,
the solvent exuding pores have a larger size than the solvent holding pores,
the solvent exuding pores are configured to exude a solvent included in the solvent exuding pores to at least one surface of the polymer gel when mechanical energy is applied to the polymer gel,
the polymeric three-dimensional network structure includes a first network structure obtained by polymerizing at least one unsaturated monomer having a charge,
the polymeric three-dimensional network structure includes a second network structure obtained by polymerizing at least one electrically neutral monomer,
the first network structure and the second network structure are entangled with each other to form the polymeric three-dimensional network structure,
a work required for elongation of the polymer gel is 3,000 J/m3 or more, as measured in a swelling state attained by swelling the polymer gel in a solvent until equilibrium,
the at least one unsaturated monomer having the charge is selected from the group consisting of 2-acrylamide-2-methylpropanesulfonic acid (AMPS), acrylic acid (AA), and methacrylic acid or a salt thereof, and
the at least one electrically neutral monomer is selected from the group consisting of acrylamide, N-isopropylacrylamide, vinyl pyridine, styrene, methyl methacrylate, a fluorine-containing monomer, hydroxyethyl acrylate, and vinyl acetate.

2. The ultrasonic diagnostic probe of claim 1, wherein the solvent exuding pores have a pore size of 0.5 µm to 1 mm.

3. The ultrasonic diagnostic probe of claim 1, wherein the polymer gel is a hydrogel comprising water as a solvent.

4. The ultrasonic diagnostic probe of claim 1, wherein the mechanical energy is at least one of a compressive force and ultrasonic waves.

5. The ultrasonic diagnostic probe of claim 1, wherein a content of the solvent in the polymer gel is 80% by weight or less, based on 100% by weight of a maximum solvent content of the polymer gel.

6. The ultrasonic diagnostic probe of claim 1, wherein the solvent exuding pores have a pore size of from 0.5 µm to 0.5 mm.

7. The ultrasonic diagnostic probe of claim 1, wherein the solvent exuding pores have a pore size of from 1 µm to 1 mm.

8. The ultrasonic diagnostic probe of claim 1, wherein the solvent exuding pores have a pore size of from 2 µm to 0.5 mm.

9. The ultrasonic diagnostic probe of claim 1, wherein the solvent holding pores have a pore size of from 200 nm or less.

10. The ultrasonic diagnostic probe of claim 1, wherein the solvent holding pores have a pore size of from 100 nm or less.

11. The ultrasonic diagnostic probe of claim 7, wherein the solvent holding pores have a pore size of from 200 nm or less.

12. The ultrasonic diagnostic probe of claim 8, wherein the solvent holding pores have a pore size of from 100 nm or less.

13. The ultrasonic diagnostic probe of claim 1, wherein the work required for elongation of the polymer gel is 4,000 J/m$^3$ or more.

14. The ultrasonic diagnostic probe of claim 1, wherein the work required for elongation of the polymer gel is 5,000 J/m$^3$ or more.

15. The ultrasonic diagnostic probe of claim 1, wherein the at least one unsaturated monomer having the charge includes 2-acrylamide-2-methylpropanesulfonic acid (AMPS) or a salt thereof.

16. The ultrasonic diagnostic probe of claim 1, wherein the at least one unsaturated monomer having the charge is selected from the group consisting of a 2-acrylamide-2-methylpropanesulfonic acid (AMPS) salt, an acrylic acid (AA) salt, and a methacrylic acid salt.

17. The ultrasonic diagnostic probe of claim 1, wherein the first network structure comprises a complex with a metal ion.

18. The ultrasonic diagnostic probe of claim 17, wherein the metal ion is selected from the group consisting of a zinc ion, an iron ion, a nickel ion, a cobalt ion, and a chromium ion.

19. The ultrasonic diagnostic probe of claim 1, wherein the neutral monomer is selected from the group consisting of N-isopropylacrylamide, vinyl pyridine, styrene, methyl methacrylate, a fluorine-containing monomer, hydroxyethyl acrylate, and vinyl acetate.

20. The ultrasonic diagnostic probe of claim 1, wherein the solvent exuding pores have a pore size of from 0.5 μm to 3 mm.

21. The ultrasonic diagnostic probe of claim 1, wherein the solvent holding pores have a pore size of 500 nm or less.

\* \* \* \* \*